United States Patent
Nomoto

(10) Patent No.: US 10,398,349 B2
(45) Date of Patent: Sep. 3, 2019

(54) ENDOSCOPE APPARATUS, ENDOSCOPE SYSTEM, AND METHOD OF DISPLAYING ENDOSCOPE IMAGE

(71) Applicant: OLYMPUS CORPORATION, Tokyo (JP)

(72) Inventor: Ryo Nomoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/935,477

(22) Filed: Mar. 26, 2018

(65) Prior Publication Data

US 2018/0286039 A1 Oct. 4, 2018

(30) Foreign Application Priority Data

Mar. 30, 2017 (JP) .................. 2017-068632

(51) Int. Cl.
| | |
|---|---|
| *A61B 5/06* | (2006.01) |
| *G06T 7/00* | (2017.01) |
| *G16H 30/40* | (2018.01) |
| *G08B 21/02* | (2006.01) |
| *A61B 5/00* | (2006.01) |
| *A61B 1/00* | (2006.01) |
| *G08B 5/22* | (2006.01) |
| *G08B 3/10* | (2006.01) |

(52) U.S. Cl.
CPC .......... *A61B 5/065* (2013.01); *A61B 1/00009* (2013.01); *A61B 1/00055* (2013.01); *A61B 5/743* (2013.01); *G06T 7/0012* (2013.01); *G08B 21/02* (2013.01); *G16H 30/40* (2018.01); *G06T 2207/10068* (2013.01); *G08B 3/10* (2013.01); *G08B 5/22* (2013.01)

(58) Field of Classification Search
CPC ........ G06T 7/0012; G06T 2207/10068; G16H 30/40; G08B 21/02; G08B 3/10; G08B 5/22; A61B 5/065

See application file for complete search history.

(56) References Cited

U.S. PATENT DOCUMENTS

| | | | | |
|---|---|---|---|---|
| 8,606,597 | B2 * | 12/2013 | Sato ....................... | G06F 19/321 705/2 |
| 2005/0196023 | A1 * | 9/2005 | Chen .................. | A61B 1/00016 382/128 |
| 2007/0226258 | A1 * | 9/2007 | Lambdin ............ | G02B 23/2469 |
| 2008/0009714 | A1 * | 1/2008 | Oda ....................... | A61B 5/065 600/424 |
| 2009/0023993 | A1 * | 1/2009 | Davidson ........... | A61B 1/00009 600/109 |

(Continued)

FOREIGN PATENT DOCUMENTS

JP 2014-018430 A 2/2014

*Primary Examiner* — John R Schnurr

(74) *Attorney, Agent, or Firm* — Scully, Scott, Murphy & Presser, P.C.

(57) ABSTRACT

An endoscope apparatus includes an image sensor configured to pick up an image of an inspection target, a display configured to display an endoscope image of the inspection target acquired by the image sensor, and a controller configured to perform notification processing to call attention of a user to the endoscope image according to an inspection history that is a history of past inspections of the inspection target and is memorized in a memory.

11 Claims, 9 Drawing Sheets

| INSPECTION TARGET | INSPECTION DATE | INSPECTION RESULT | DAMAGE INFORMATION |
|---|---|---|---|
| A | INSPECTION DATE 1 | REINSPECTION REQUIRED | CRACK |
| A | INSPECTION DATE 2 | CAUTION NEEDED | DEPRESSION |
| A | INSPECTION DATE 3 | NO PROBLEM | |
| A | INSPECTION DATE 4 | NO PROBLEM | |
| A | INSPECTION DATE 5 | NO PROBLEM | |
| B | INSPECTION DATE 6 | NO PROBLEM | |
| C | INSPECTION DATE 7 | NOT INPUTTED YET | |
| ⋮ | ⋮ | ⋮ | ⋮ |

T2

(56) References Cited

U.S. PATENT DOCUMENTS

| | | | | |
|---|---|---|---|---|
| 2011/0301447 A1* | 12/2011 | Park | .................... | G06T 7/0016 |
| | | | | 600/407 |
| 2012/0221569 A1* | 8/2012 | Sato | .................... | G06F 19/321 |
| | | | | 707/736 |
| 2013/0342667 A1* | 12/2013 | Miyayashiki | .......... | H04N 5/765 |
| | | | | 348/65 |
| 2013/0345502 A1* | 12/2013 | Mitsunaga | ........... | A61B 1/0002 |
| | | | | 600/103 |
| 2014/0024891 A1* | 1/2014 | Motoki | ............. | A61B 1/00045 |
| | | | | 600/103 |
| 2015/0313445 A1* | 11/2015 | Davidson | ............. | G06T 3/4038 |
| | | | | 600/109 |
| 2016/0235340 A1* | 8/2016 | Sidar | .................... | A61B 5/065 |
| 2018/0108439 A1* | 4/2018 | Sato | .................... | G06F 19/321 |

\* cited by examiner

| INSPECTION TARGET | INSPECTION DATE | INSPECTION RESULT | DAMAGE INFORMATION |
|---|---|---|---|
| A | INSPECTION DATE 1 | REINSPECTION REQUIRED | CRACK |
| A | INSPECTION DATE 2 | CAUTION NEEDED | DEPRESSION |
| A | INSPECTION DATE 3 | NO PROBLEM | |
| A | INSPECTION DATE 4 | NO PROBLEM | |
| A | INSPECTION DATE 5 | NO PROBLEM | |
| B | INSPECTION DATE 6 | NO PROBLEM | |
| C | INSPECTION DATE 7 | NOT INPUTTED YET | |
| ⋮ | ⋮ | ⋮ | ⋮ |

ENDOSCOPE APPARATUS, ENDOSCOPE SYSTEM, AND METHOD OF DISPLAYING ENDOSCOPE IMAGE

CROSS-REFERENCE TO RELATED APPLICATIONS

This application is based upon and claims the benefit of priority from the Japanese Patent Application No. 2017-068632, filed Mar. 30, 2017; the entire contents of which are incorporated herein by reference.

BACKGROUND

1. Technical Field

The present invention relates to an endoscope apparatus, an endoscope system, and a method of displaying an endoscope image.

2. Background Art

An existing endoscope system memorizes an endoscope image used in inspection work and displays the endoscope image memorized during the inspection work, after inspection. For example, Japanese Patent Application Laid-Open Publication No. 2014-18430 discloses an endoscope system that receives coordinate information of a region of interest where abnormality has been detected during the inspection work, memorizes the endoscope image and the coordinate information of the region of interest, and superimposes an indicator indicating the region of interest on a position indicated in the coordinate information to reproduce the endoscope image, in order to increase efficiency of validation work of the inspection result.

SUMMARY

An endoscope apparatus according to an aspect of the present invention includes an image sensor configured to pick up an image of an inspection target, a display configured to display an endoscope image of the inspection target acquired by the image sensor, and a controller configured to perform notification processing to call attention of a user to the endoscope image according to an inspection history that is a history of past inspections of the inspection target and is memorized in a memory.

An endoscope system according to an aspect of the present invention includes an endoscope apparatus, and an information management apparatus configured to be connected to the endoscope apparatus through a network. The endoscope apparatus includes an image sensor, a display, and a controller. The image sensor picks up an image of an inspection target. The display displays an endoscope image of the inspection target acquired by the image sensor. The controller outputs, to the information management apparatus, the inspection target and a predetermined condition for determination of notification processing, instructs the information management apparatus to perform determination processing of whether to perform the notification processing, and performs the notification processing to call attention of a user to the endoscope image, according to a determination result inputted from the information management apparatus. The information management apparatus outputs, to the endoscope apparatus, the determination result indicating execution of the notification processing when an amount of inspection results each indicating abnormality of the inspection target in an inspection history satisfies the predetermined condition according to the instruction, and the inspection history is a history of past inspections of the inspection target.

A method of displaying an endoscope image according to an aspect of the present invention includes picking up, by an image sensor, an image of an inspection target, displaying, by a display, an endoscope image of the inspection target acquired by the image sensor, and performing, by a controller, notification processing to call attention of a user to the endoscope image, according to an inspection history that is a history of past inspections of the inspection target and is memorized in a memory.

DETAILED DESCRIPTION OF THE PREFERRED EMBODIMENT

An embodiment of the present invention is described below with reference to drawings.

(Configuration)

Figure 1:
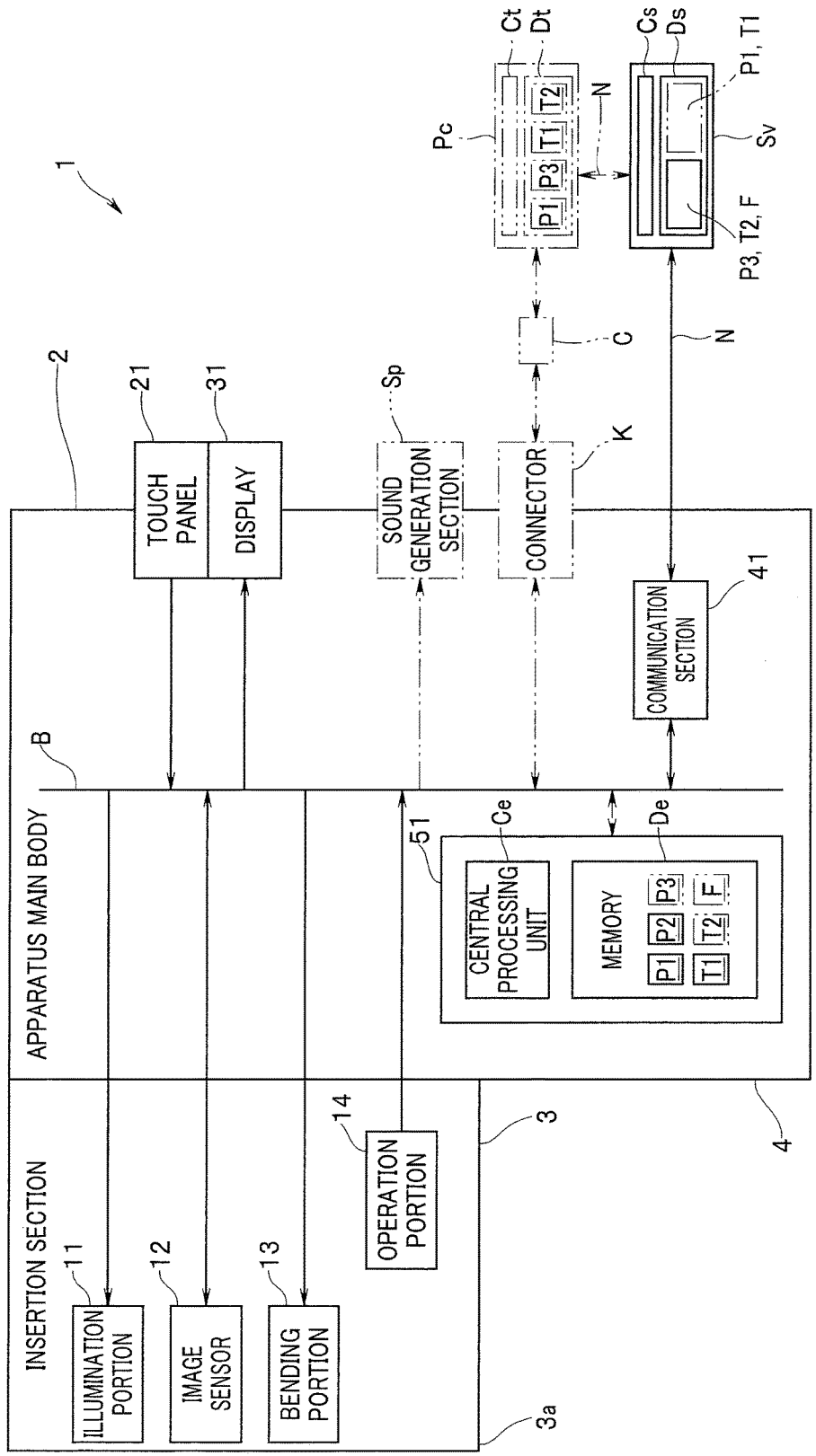
FIG. 1 is a block diagram illustrating an example of a configuration of an endoscope system according to an embodiment of the present invention.

FIG. 1 is a block diagram illustrating an example of a configuration of an endoscope system 1 according to the embodiment of the present invention.

The endoscope system 1 includes an endoscope apparatus 2 and an information management apparatus Sv. The endoscope apparatus 2 is connected to the information management apparatus Sv through a network N such as the internet and LAN.

The endoscope apparatus 2 includes an insertion section 3 and an apparatus main body 4. Sections inside the endoscope apparatus 2 are connected to one another through an internal wiring B.

The insertion section 3 is formed in an elongated shape and is configured to be inserted into an object as an inspection target from a distal end portion 3a side. A proximal end of the insertion section 3 is detachably connected to the apparatus main body 4. The insertion section 3 includes an illumination portion 11, an image sensor 12, a bending portion 13, and an operation portion 14. Note that the distal end portion 3a may have a configuration from which an unillustrated optical adaptor is detachable.

The illumination portion 11 is configured to illuminate the inspection target. The illumination portion 11 includes a light emitting device such as an LED. The illumination portion 11 is connected to a controller 51 of the apparatus main body 4 and applies illumination light from the distal end portion 3a to the object under control of the controller 51.

The image sensor 12 is configured to pick up an image of the inspection target. The image sensor 12 includes an image pickup device such as a CCD and a CMOS, and an image pickup optical system such as a lens disposed on image pickup surface side of the image pickup device. The image sensor 12 is connected to the controller 51 and acquires an image of the object as the inspection target under control of the controller 51.

The bending portion 13 is provided on the proximal end side of the distal end portion 3a. The bending portion 13 is connected to an unillustrated bending drive portion through a wire. The bending portion 13 bends the insertion section 3 through advancing and retreating of the wire under control of the controller 51.

The operation portion 14 is configured to allow instruction input. The operation portion 14 include various kinds of unillustrated operation tools such as a joystick, a freeze button, a recording instruction button, and a vertical and horizontal direction bending button. The operation portion 14 is connected to the controller 51, and outputs, to the controller 51, a control signal corresponding to the instruction input. In other words, the operation portion 14 is an instruction input portion.

The apparatus main body 4 includes a touch panel 21, a display 31, a communication section 41, and the controller 51.

The touch panel 21 is configured to allow instruction input. The touch panel 21 is superimposed on the display 31, and outputs, to the controller 51, a control signal corresponding to the instruction input. In other words, the touch panel 21 is the instruction input portion.

The display 31 includes, for example, an LCD. The display 31 displays various kinds of images, for example, a set image Cf (FIG. 6), live images L1, L2, L2a, and L3 (FIG. 8 to FIG. 11) of the endoscope image based on the image of the object as the inspection target acquired by the image sensor 12, notification images H1 and 112 (FIG. 9 to FIG. 11), and reproduction images.

The communication section 41 is configured to be connected to the information management apparatus Sv through the network N, under control of the controller 51.

Figure 2:
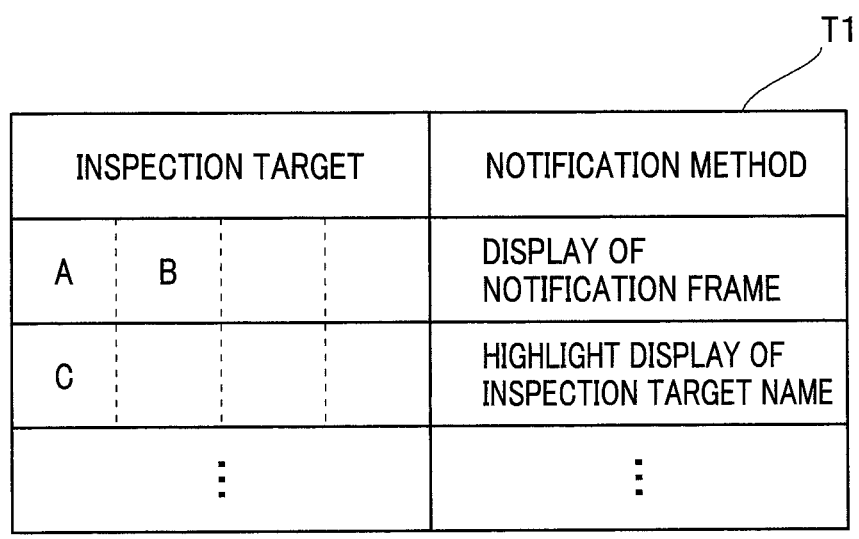
FIG. 2 is a table illustrating an example of a notification method table of the endoscope system according to the embodiment of the present invention.

FIG. 2 is a table illustrating an example of a notification method table T1 of the endoscope system 1 according to the embodiment of the present invention.

The controller 51 can control various kinds of operation in the endoscope apparatus 2. The controller 51 includes a central processing unit Ce and a memory De that is read or written by the central processing unit Ce.

The central processing unit Ce can execute various kinds of processing. The function of the controller 51 is realized when the central processing unit Ce executes various kinds of programs memorized in the memory De.

The memory De includes a RAM and a rewritable flash ROM. The notification method table T1 and programs of a setting processing portion P1 and a notification processing portion P2 are also memorized in the memory De. The notification method table T1 includes information of the inspection target and the notification method associated with the inspection target. In the example of FIG. 2, the notification method corresponding to inspection targets A and B is "display of notification frame", and the notification method corresponding to an inspection target C is "highlight display of inspection target name".

The setting processing portion P1 outputs, to the information management apparatus Sv, the inspection target and a predetermined condition for determination of notification processing, instructs the information management apparatus Sv to perform determination processing of whether to perform the notification processing, and performs setting of the notification method table T1 based on a determination result inputted from the information management apparatus Sv. The predetermined condition is instructed and inputted by a user.

The notification processing portion P2 performs the notification processing with use of the notification method corresponding to the inspection target, based on the notification method table T1. In other words, the controller 51 displays a notification image on the display 31 to give notification to the user.

Figure 3:
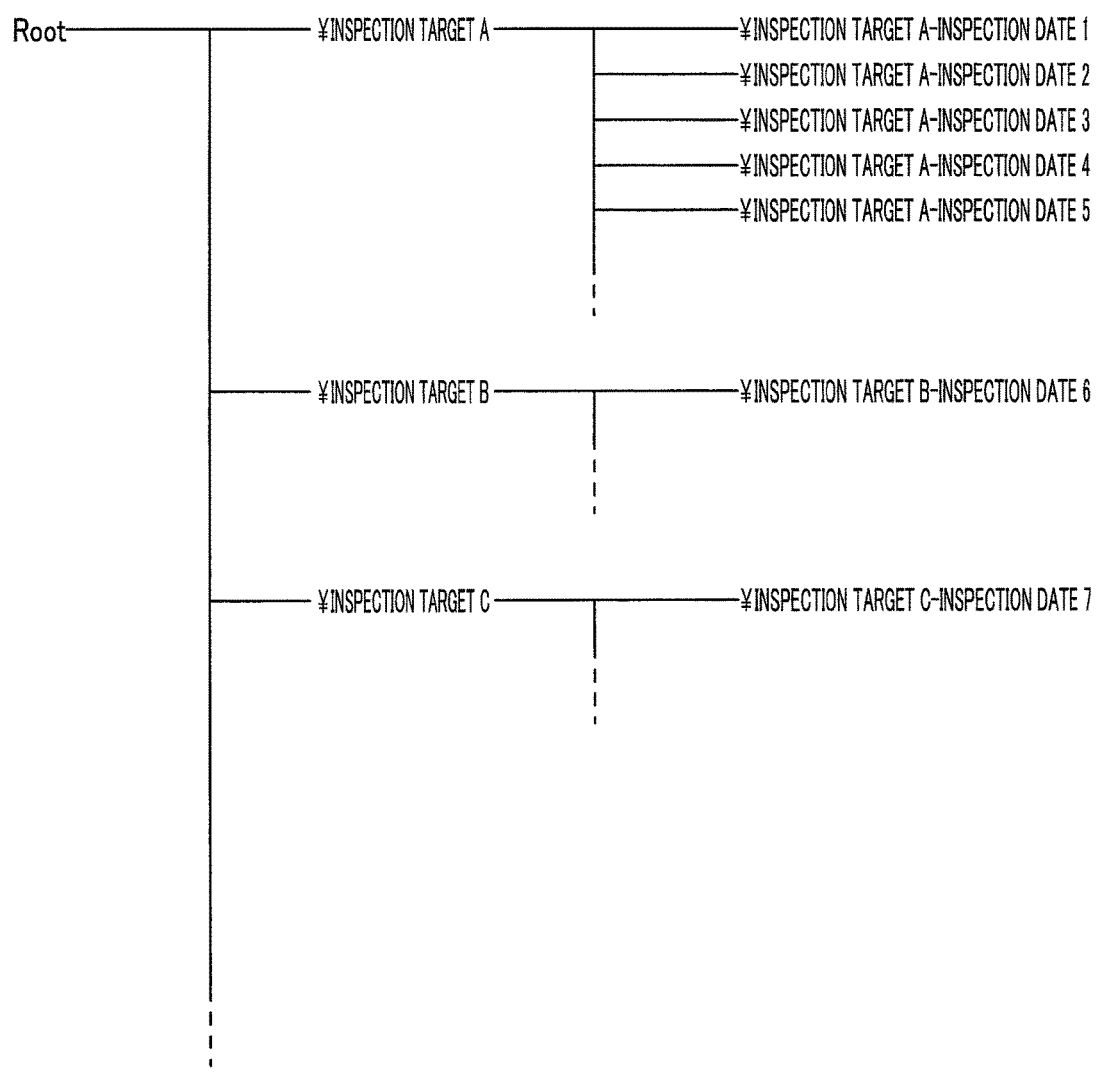
FIG. 3 is a diagram illustrating an example of a hierarchical structure of folders of inspection information of the endoscope system according to the embodiment of the present invention.
Figure 4:
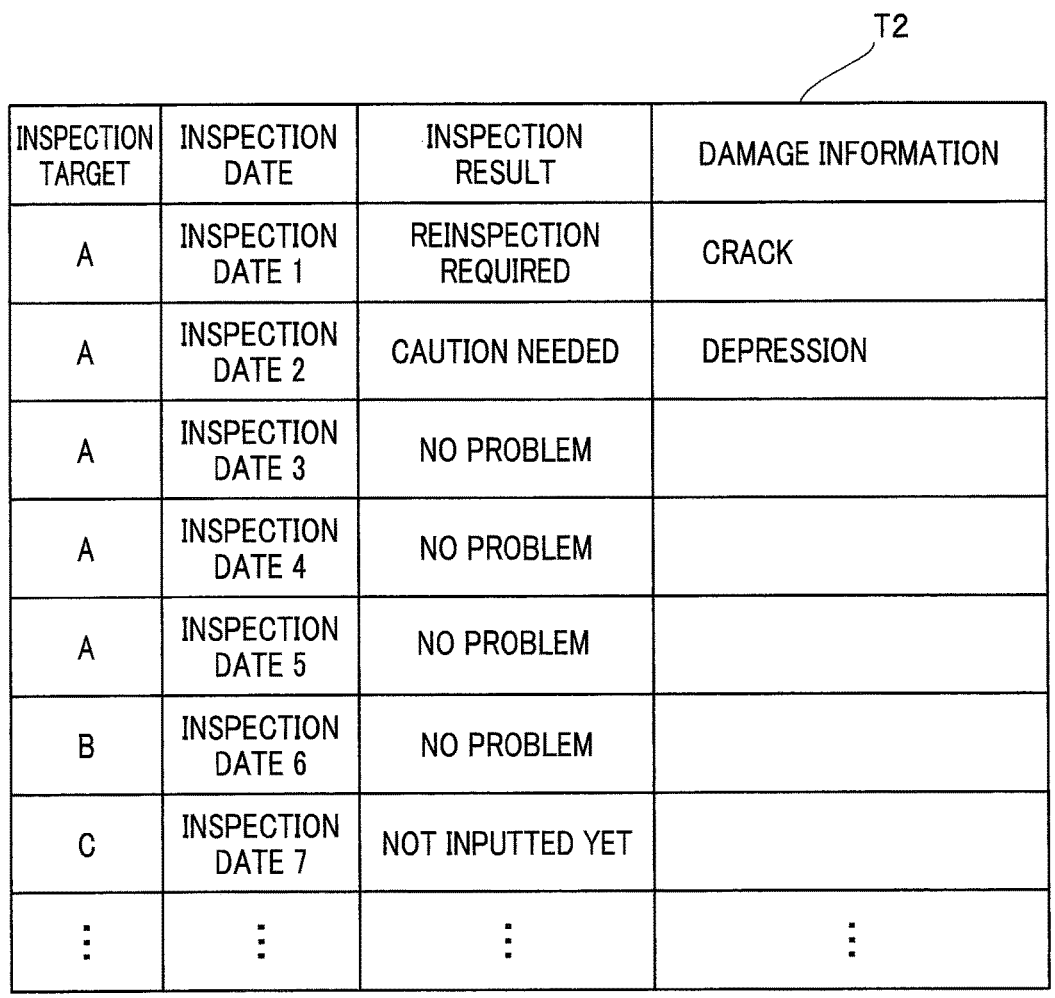
FIG. 4 is a table illustrating an example of an inspection history table of the endoscope system according to the embodiment of the present invention.

FIG. 3 is a diagram illustrating an example of a hierarchical structure of folders of inspection information F of the endoscope system 1 according to the embodiment of the present invention. FIG. 4 is a table illustrating an example of an inspection history table T2 of the endoscope system 1 according to the embodiment of the present invention.

The information management apparatus Sv is, for example, a server. The information management apparatus Sv includes a central processing unit Cs and a memory Ds. The inspection information F, the inspection history table T2, and the programs of the determination processing portion P3 are memorized in the memory Ds.

The inspection information F is information acquired through inspection work. The inspection information F includes inspection files that are held by the folders in the hierarchical structure. For example, in FIG. 3, folders "inspection target A", "inspection target B", and "inspection target C" each indicating the inspection target are included in a lower hierarchy of "Root". Further, an inspection file named by the inspection target and an inspection date is stored in each of the folders for each inspection date. Moreover, inspection files "inspection target A-inspection date 1" to "inspection target A-inspection date 5" are stored in the folder "inspection target A", an inspection file "inspection target B-inspection date 6" is stored in the folder "inspection target B", and an inspection file "inspection target C-inspection date 7" is stored in the folder "inspection target C". In other words, the inspection result of the inspection work is stored in the folder named according to the inspection target, of the memory Ds. Note that the hierarchical structure of the folders in FIG. 3 is illustrative and is a non-limiting one.

The inspection file includes a still endoscope image or a moving endoscope image. The inspection file includes the inspection result and damage information that are instructed and inputted by the user, in addition to the endoscope image.

Out of information "reinspection required", "caution needed", "no problem", and "not inputted yet" indicating a state that the result has not been inputted yet, the information instructed and inputted by the user is set to the inspection result.

Information, of damage detected through the inspection work, instructed and inputted by the user is set to the damage information. For example, when the inspection work of the inspection target A is performed on the inspection date 1 and crack Cr (FIG. 10) is detected, the user operates the instruction input portion to instruct and input the inspection result "reinspection required" and the damage information "crack".

As illustrated in FIG. 4, the inspection history table T2 includes an inspection history that includes the inspection target, the inspection date, the inspection result, and the damage information. For example, as for the inspection target A, the inspection result is "reinspection required" and the damage information is "crack" on the inspection date 1, the inspection result is "caution needed" and the damage information is "depression" on the inspection date 2, and the inspection result is "no problem" on the inspection dates 3 to 5. As for the inspection target B, the detection result is "no problem" on the inspection date 6. As for the inspection target C, the inspection result is "not inputted yet" on the inspection date 7.

In other words, the memory Ds includes the inspection history table T2 as a table of the inspection history, and the inspection history table T2 includes the inspection targets and the inspection results respectively associated with the inspection targets.

The terms "reinspection required" and "caution needed" in FIG. 4 are inspection results each indicating abnormality of the inspection target.

Note that the terms "reinspection required", "caution needed", "no problem", and "not inputted yet" of the detection results are illustrative and non-limiting ones.

When the inspection file is inputted from the endoscope apparatus 2 through the communication section 41, the information management apparatus Sv updates the inspection information F and the inspection history table T2.

The determination processing portion P3 is operated by the central processing unit Cs. When an amount of the inspection results each indicating abnormality of the inspection target in the inspection history satisfies a predetermined condition, according to the inspection history of the inspection history table T2, the determination processing portion P3 outputs a determination result that indicates execution of the notification processing.

In response to the determination result, the endoscope apparatus 2 outputs the inspection target and the predetermined condition for determination of the notification processing and instructs the information management apparatus Sv to perform the determination processing of whether to perform the notification processing. When the amount of the inspection results each indicating abnormality of the inspection target in the inspection history satisfies the predetermined condition, according to the inspection history of the inspection history table T2 memorized in the memory Ds, the information management apparatus Sv outputs, to the endoscope apparatus 2, the determination result in which control information for execution of the notification processing is set. The endoscope apparatus 2 performs the notification processing to call attention of the user to the endoscope image, based on the determination result.

In other words, the controller 51 performs the notification processing to call attention of the user to the endoscope image, according to the inspection history that is a history of past inspections of the inspection target memorized in the memory Ds. More specifically, when the amount of the inspection results each indicating abnormality of the inspection target in the inspection history satisfies the predetermined condition, the controller 51 sets, in the notification method table T1, the inspection target and the predetermined notification method associated with the inspection target and performs the notification processing based on the notification method table T1.

(Operation)

Subsequently, the setting processing of the endoscope system 1 is described.

Figure 5:
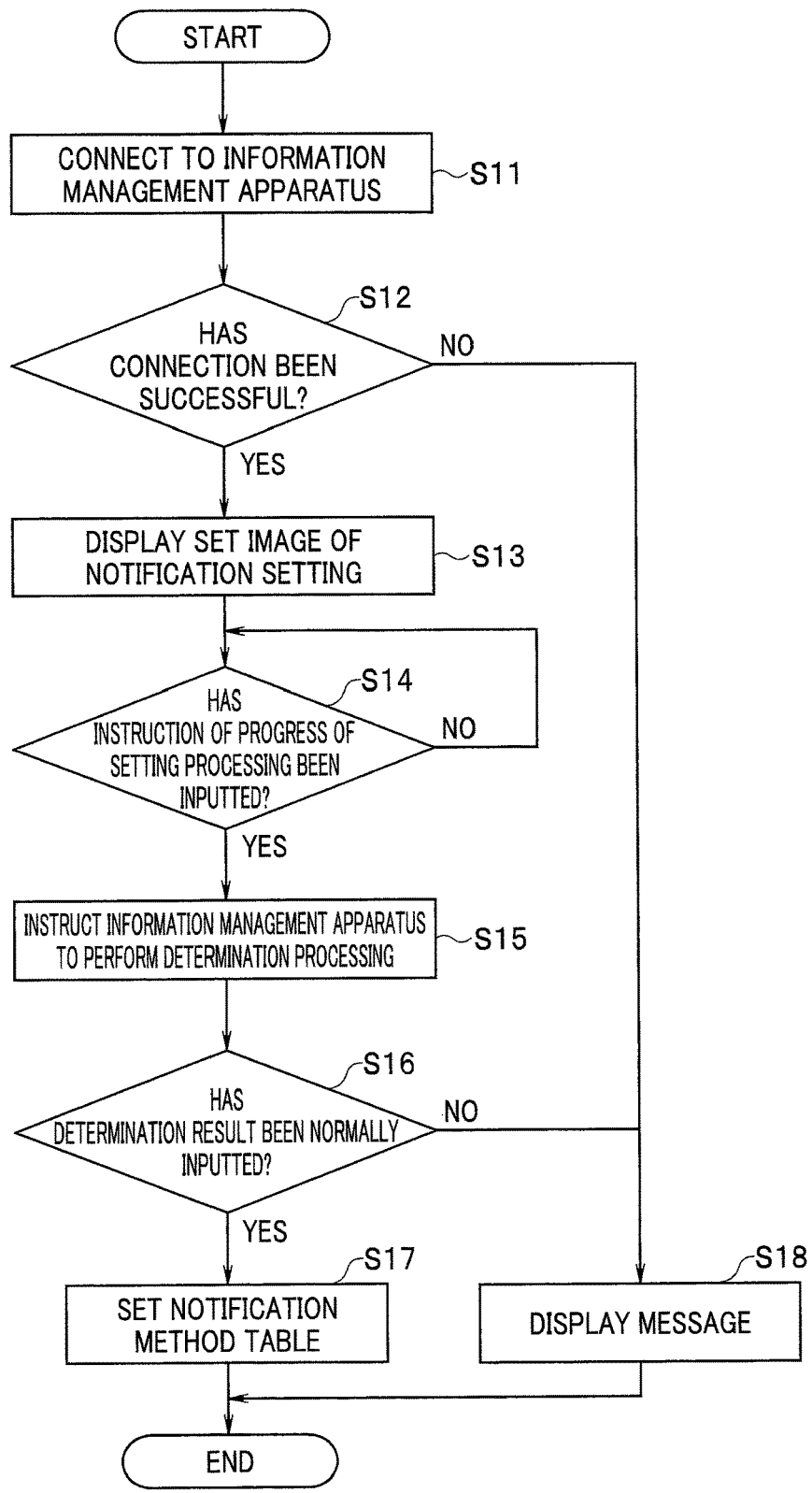
FIG. 5 is a flowchart illustrating an example of a flow of setting processing of the endoscope system according to the embodiment of the present invention.
Figure 6:
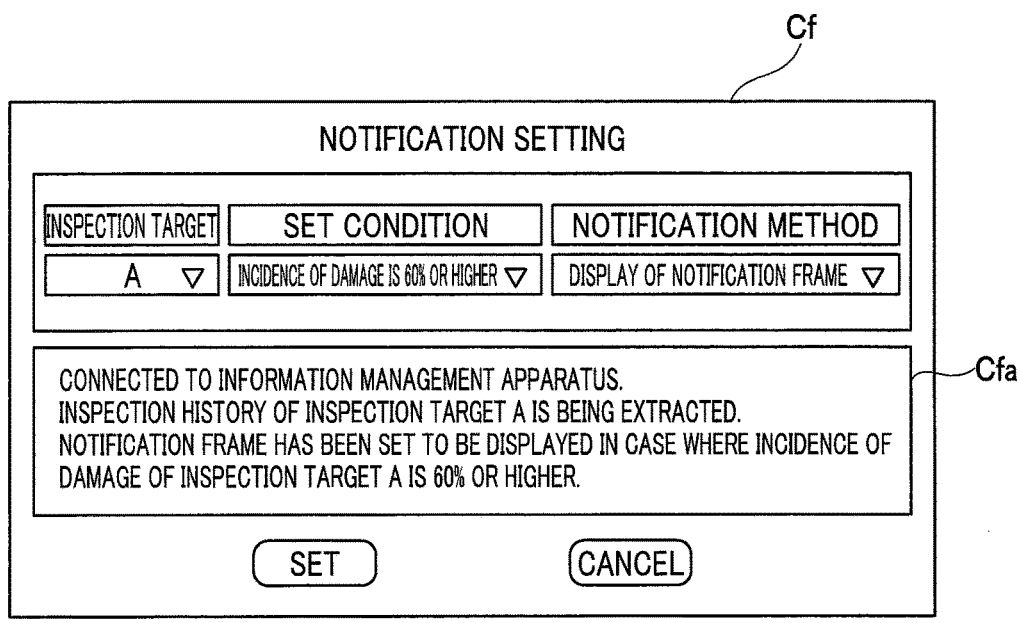
FIG. 6 is a diagram illustrating a display example of a set image of the endoscope system according to the embodiment of the present invention.

FIG. 5 is a flowchart illustrating an example of a flow of the setting processing of the endoscope system 1 according to the embodiment of the present invention. FIG. 6 is a diagram illustrating a display example of a set image Cf of the endoscope system 1 according to the embodiment of the present invention.

When start of the setting processing is instructed and inputted through the instruction input portion, the controller 51 starts the setting processing.

The endoscope apparatus 2 is connected to the information management apparatus Sv (step S11). The controller 51 connects to the information management apparatus Sv through the communication section 41.

It is determined whether the connection has been successful (step S12). When the controller 51 determines that the connection has not been successful, the processing proceeds to step S18. In contrast, when the controller 51 determines that the connection has been successful, the processing proceeds to step S13.

The set image Cf of the notification setting is displayed (step S13). The controller 51 displays the set image Cf illustrated in FIG. 6, on the display 31. The operation image for instruction input of "inspection target", "set condition", "notification method", "set", and "cancel" is displayed in the set image Cf. The user can instruct and input the inspection target, the set condition, and the notification method through the instruction input portion. FIG. 6 illustrates an example in which the inspection target "A", the set condition "incidence of damage is 60% or higher", and the notification method "display of notification frame" are instructed and inputted through operation of a pull-down menu.

It is determined whether instruction of progress of the setting processing has been inputted (step S14). The user operates "set" in the operation image to input instruction of progress of the setting processing. The process in step S14 is repeated until the controller 51 determines that the instruction of progress of the setting processing has been inputted. When the controller 51 determines that the instruction of progress of the setting processing has been inputted, the processing proceeds to step S15.

The determination processing is instructed to the information management apparatus Sv (step S15). The controller 51 outputs the inspection target and the predetermined condition to the information management apparatus Sv through the communication section 41, to perform instruction of the determination processing. The predetermined condition is determined according to the set condition instructed and inputted in step S13. When the instruction of the determination processing is inputted, the information management apparatus Sv outputs a determination result of the processing by the determination processing portion P3, based on the inspection target and the predetermined condition. More specifically, the information management apparatus Sv extracts, from the inspection history table T2, the inspection history of the inspection target of a predetermined period. Subsequently, the information management apparatus Sv calculates a ratio of the inspection result "reinspection required" or "caution needed" in the extracted inspection history. Thereafter, when the calculated ratio satisfies a predetermined condition, the information management apparatus Sv sets the control information for execution of the notification processing in the determination result and outputs the determination result to the endoscope apparatus 2. The predetermined period is empirically or experimentally set in advance in order to output a favorable determination result.

For example, in a case where the predetermined period is set to a period of the inspection date 1 to the inspection date 3, when the instruction input is performed as illustrated in FIG. 6, the information management apparatus Sv extracts the inspection history of the inspection date 1 to the inspection date 3. Subsequently, the information management apparatus Sv calculates the ratio of the inspection result "reinspection required" or "caution needed" in the inspection history, as 66%. Thereafter, the information management apparatus Sv sets, in the determination result, the control information for execution of the notification processing, and outputs the determination result to the endoscope apparatus 2.

When the extracted inspection history does not satisfy the predetermined condition, the information management apparatus Sv sets, in the determination result, the control information for not executing the notification processing, and outputs the determination result to the endoscope apparatus 2. Further, when an error occurs, the information management apparatus Sv sets, in the determination result, the control information indicating error, and outputs the determination result to the endoscope apparatus 2.

It is determined whether the determination result has been normally inputted (step S16). When the determination result is inputted from the information management apparatus Sv, the controller 51 determines whether the determination result has been normally inputted. When the control information indicating error is set in the determination result, the processing proceeds to step S18. In contrast, when the control information for execution of the notification processing or the control information for not executing the notification processing is set in the determination result, the processing proceeds to step S17.

Setting of the notification method table T1 is performed (step S17). When the control information for not executing the notification processing is inputted from the information management apparatus Sv in step S16, the controller 51 sets the notification method table T1 so as not to include the inspection target. In contrast, when the control information for execution of the notification processing is inputted, the controller 51 associates identification information of the inspection target with the notification method instructed and inputted in step S13, and sets the identification information and the notification method in the notification method table T1. After the setting of the notification method table T1, the setting processing ends.

A message is displayed (step S18). The controller 51 displays a message in a message region Cfa. For example, when connection with the information management apparatus Sv is not successful in step S12, the controller 51 displays a message, for example, "connection with information management apparatus has not been successful" in the message region Cfa. In addition, when the control information indicating error is inputted from the information management apparatus Sv in step S16, the controller 51 displays a message, for example, "error has occurred" in the message region Cfa. After step S18 ends, the setting processing ends.

As illustrated in FIG. 6, various kinds of messages are displayed in the message region Cfa in addition to the message in step S18, according to a progress situation of the setting processing.

The processes in steps S11 to S18 configure the setting processing.

Note that, to maintain the notification method table T1 in the latest state, the processes in steps S15 to S18 may be executed at respective predetermined timing, for example, at a time when the endoscope apparatus 2 is turned on.

Subsequently, the notification processing of the endoscope system 1 is described.

Figure 7:
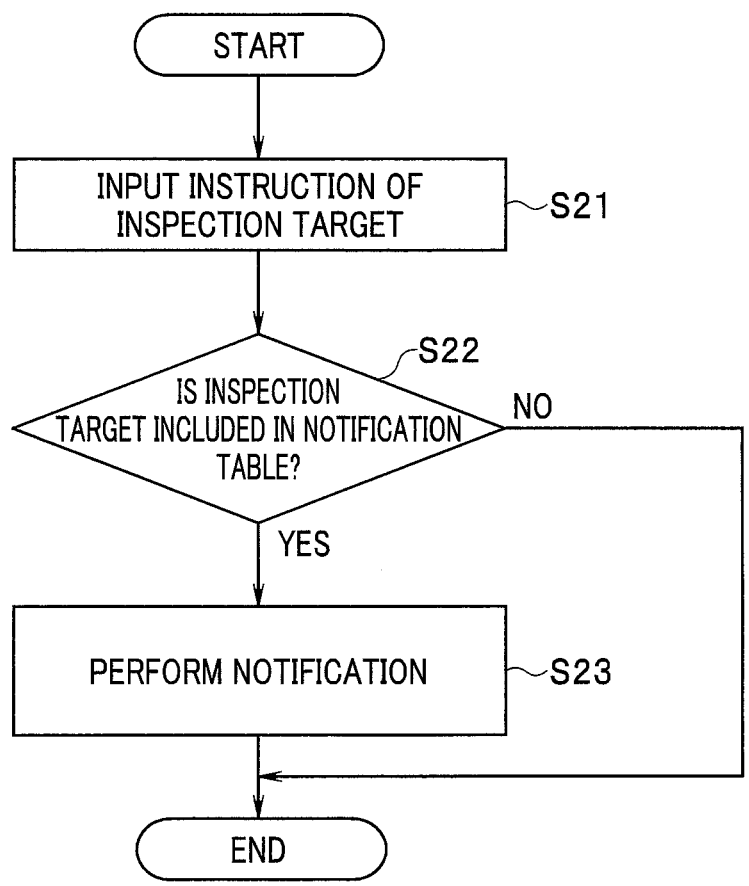
FIG. 7 is a flowchart illustrating an example of a flow of notification processing of the endoscope system according to the embodiment of the present invention.

FIG. 7 is a flowchart illustrating an example of a flow of the notification processing of the endoscope system 1 according to the embodiment of the present invention. FIG. 8 to FIG. 11 are diagrams respectively illustrating display examples of live images L1, L2, L2a, and L3 of the endoscope system 1 according to the embodiment of the present invention. In FIG. 8 to FIG. 11, a turbine blade of a gas turbine is illustrated.

When the user inputs an instruction of live display through operation of the instruction input portion, the notification processing is started.

The instruction of the inspection target is inputted (step S21). The controller 51 displays a message on the display 31 to prompt the user to input the instruction of the inspection target. When the user inputs the instruction of the inspection target, the processing proceeds to step S22.

It is determined whether the inspection target is included in the notification method table T1 (step S22). When the controller 51 determines that the inspection target is not included in the notification method table T1, the processing ends. In contrast, when the controller 51 determines that the inspection target is included in the notification method table T1, the processing proceeds to step S23.

Notification is performed (step S23). The controller 51 performs notification corresponding to the inspection target, based on the notification method table T1.

Figure 8:
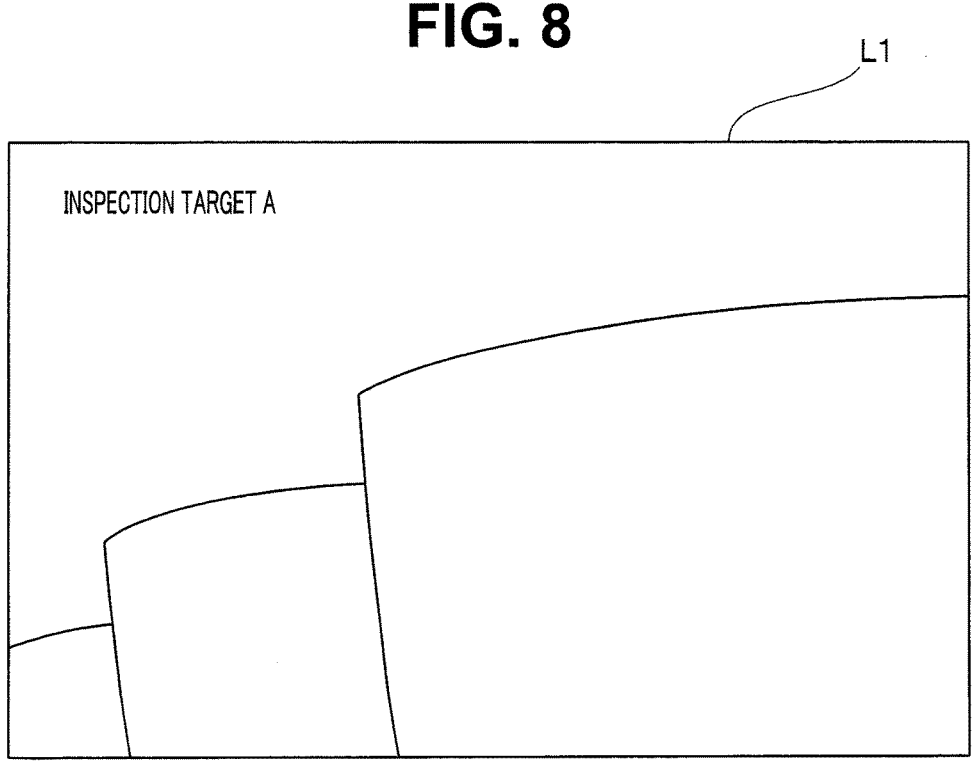
FIG. 8 is a diagram illustrating a display example of a live image of the endoscope system according to the embodiment of the present invention.
Figure 9:
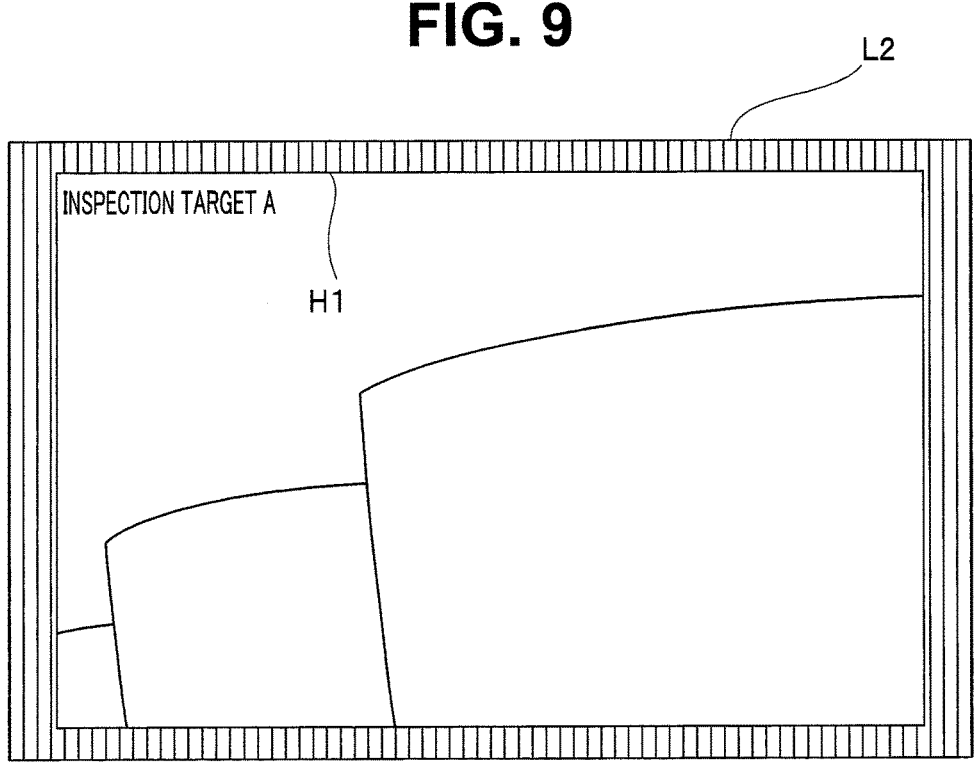
FIG. 9 is a diagram illustrating a display example of the live image of the endoscope system according to the embodiment of the present invention.
Figure 10:
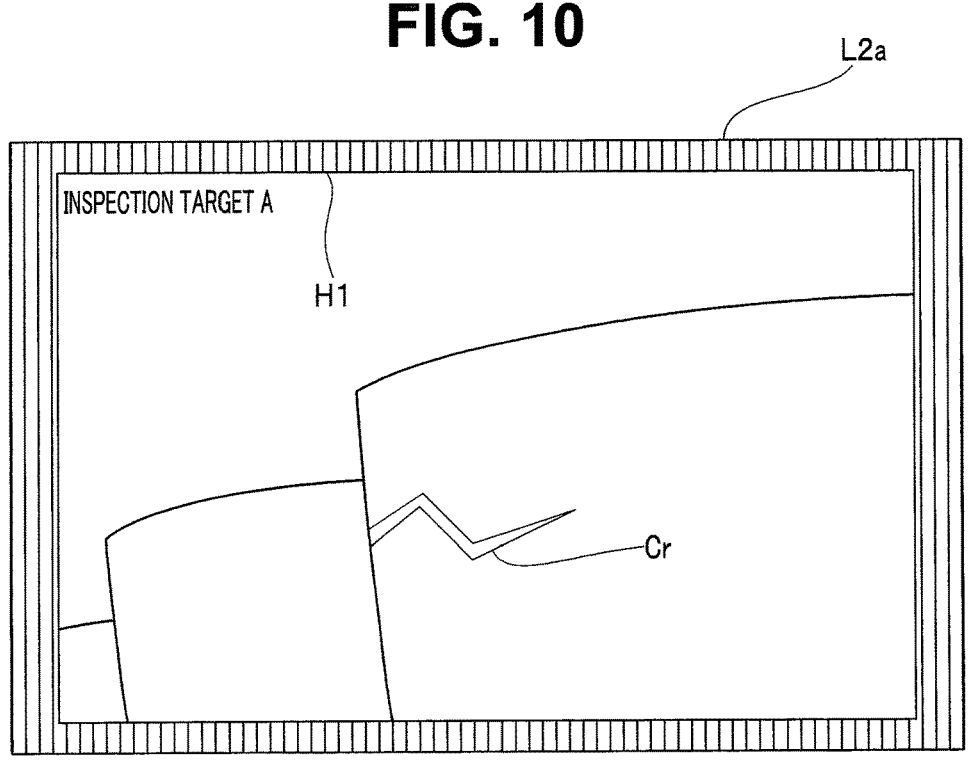
FIG. 10 is a diagram illustrating a display example of the live image of the endoscope system according to the embodiment of the present invention.

In display of the notification frame, the controller 51 displays a notification image H1 with, for example, a red frame pattern on a peripheral edge of the live image L1 of FIG. 8 not including the notification image, as an example of the live image L2 of FIG. 9 and the live image L2a including crack Cr of FIG. 10.

Figure 11:
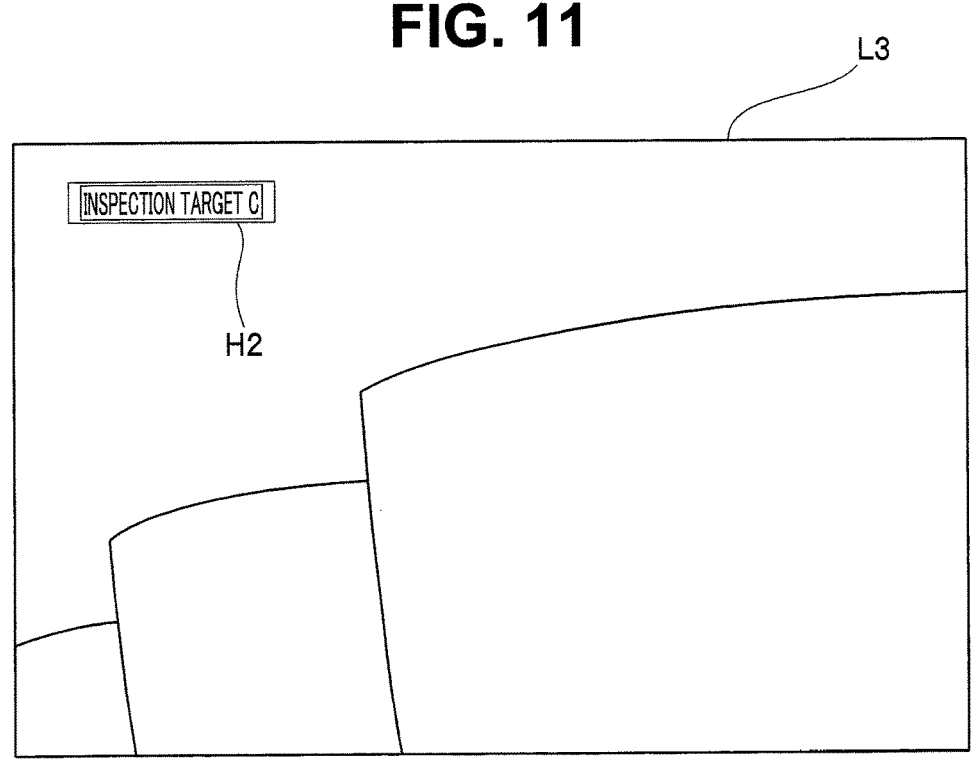
FIG. 11 is a diagram illustrating a display example of the live image of the endoscope system according to the embodiment of the present invention.

In highlight display of inspection target name, as illustrated in an example of the live image L3 of FIG. 11, the controller 51 displays a notification image H2 with a frame pattern in a periphery of the inspection target name displayed on the display 31, thereby highlight displaying the inspection target name.

The processes in steps S21 to S23 configure the notification processing.

In other words, in a method of displaying the endoscope image, an image of the inspection target is picked up by the image sensor 12, the endoscope image of the inspection target acquired by the image sensor 12 is displayed by the display 31, and the controller 51 performs the notification processing to call attention of the user to the endoscope image, according to the inspection history of the inspection history table T2 memorized in the memory Ds. The notification processing is performed when the amount of the detection results each indicating abnormality of the inspection target in the inspection history satisfies the predetermined condition.

According to the above-described embodiment, the endoscope system 1 makes it possible to notify the user of possibility of abnormality such as damage on the inspection target, and to cause the user to more efficiently detect the region in which the abnormality occurs in the inspection target.

Modification of Embodiment

In the embodiment, the inspection file is outputted to the information management apparatus Sv through the communication section 41; however, the inspection file may be outputted to the information management apparatus Sv through a memory card C and a terminal device Pc. In description of the present modification, description of the components same as the components in the embodiment is omitted.

The endoscope system 1 includes a connector K, the memory card C, and the terminal device Pc. The terminal device Pc is connected to the information management apparatus Sv through the network N (alternate long and two short dashes line in FIG. 1).

The connector K is configured to be attached with the memory card C. When the memory card C is attached to the connector K, the controller 51 can perform reading and writing of the memory card C.

The terminal device Pc is configured to perform reading and writing of the memory card C. When the inspection file is read from the memory card C, the terminal device Pc outputs, to the information management apparatus Sv, the inspection target, the inspection date, the inspection result, and the damage information.

Note that, in the embodiment and the modification, the determination processing portion P3, the inspection history table T2, and the inspection information F are memorized in the information management apparatus Sv, and the determination processing is performed by the information management apparatus Sv. Alternatively, the determination processing portion P3, the inspection history table T2, and the inspection information F may be memorized in the memory De, and the determination processing may be performed by the central processing unit Ce (alternate long and two short dashes line in memory De of FIG. 1).

Note that, in the embodiment and the modification, the determination processing portion P3 and the inspection history table T2 are memorized in the information management apparatus Sv, and the determination processing is performed by the information management apparatus Sv. Alternatively, the determination processing portion P3 and the inspection history table T2 may be memorized in a memory Dt inside the terminal device Pc, and the determination processing may be performed by a central processing unit Ct (alternate long and two short dashes line in memory Dt of FIG. 1).

Note that, in the embodiment and the modification, the setting processing portion P1 and the notification method table T1 are memorized in the memory De. Alternatively, the notification method table T1 may be memorized in the memories Ds and Dt, and the controller 51 may read the notification method table T1 in the memories Ds and Dt to perform the notification processing (alternate long and two short dashes line in memories Ds and Dt of FIG. 1).

Note that, in the embodiment and the modification, the highlight display of the inspection target name is performed by the notification image H2 with the frame pattern around the inspection target name displayed on the display 31. Alternatively, the highlight display may be performed through change of a color of characters of the inspection target name.

Note that, in the embodiment and the modification, the examples in which the notification processing is performed through the notification methods of "display of notification frame" and "highlight display of inspection target name" have been described. Alternatively, the notification processing may be performed through the other notification method.

Note that, in the embodiment and the modification, one notification method is set for one inspection target as an example. Alternatively, a plurality of notification methods may be set for one inspection target. For example, setting may be performed as for one inspection target such that the notification processing is performed through a first notification method when "incidence of damage is 60% or higher", and the notification processing is performed through a second notification method when "incidence of damage is less than 60%".

Note that, in the embodiment and the modification, the controller 51 performs the notification processing with use of the notification images H1 and H2 displayed on the display 31. Alternatively, the notification processing may be performed with use of a notification sound generated by a sound generation section Sp (alternate long and two short dashes line in FIG. 1).

The present invention is not limited to the embodiment and the modification described above and may be variously modified or alternated without departing from the scope of the present invention.

What is claimed is:

1. An endoscope apparatus, comprising:
    an image sensor configured to pick up an image of an inspection target;
    a display configured to display an endoscope image of the inspection target acquired by the image sensor; and
    a controller configured to perform notification processing to call attention of a user to the endoscope image according to an inspection history that is a history of past inspections of the inspection target and is memorized in a memory;
    wherein the controller performs the notification processing when an amount of inspection results each indicating abnormality of the inspection target in the inspection history satisfies a predetermined condition.

2. The endoscope apparatus according to claim 1, wherein the memory stores an inspection history table as a table of the inspection history, and
    the inspection history table includes the inspection target and the inspection result associated with the inspection target.

3. The endoscope apparatus according to claim 1, wherein the controller sets, in a notification method table that includes the inspection target and a notification method associated with the inspection target, the inspection target and a predetermined notification method associated with the inspection target, and performs the notification processing with use of the notification method corresponding to the inspection target, based on the notification method table, when the amount of inspection results each indicating abnormality of the inspection target in the inspection history satisfies the predetermined condition.

4. The endoscope apparatus according to claim 1, wherein the inspection result is stored in a folder of the memory named corresponding to the inspection target.

5. The endoscope apparatus according to claim 1, wherein the endoscope image is a live image.

6. The endoscope apparatus according to claim 1, further comprising an instruction input portion, wherein the predetermined condition is instructed and inputted through the instruction input portion.

7. The endoscope apparatus according to claim 1, wherein the controller displays a notification image on the display to give notification to the user.

8. The endoscope apparatus according to claim 1, wherein the controller is configured to generate a notification sound to give notification to the user.

9. An endoscope system, comprising:
an endoscope apparatus; and
an information management apparatus configured to be connected to the endoscope apparatus through a network, wherein
the endoscope apparatus includes an image sensor, a display, and a controller, the image sensor picking up an image of an inspection target, the display displaying an endoscope image of the inspection target acquired by the image sensor, and the controller outputting, to the information management apparatus, the inspection target and a predetermined condition for determination of notification processing, instructing the information management apparatus to perform determination processing of whether to perform the notification processing, and performing the notification processing to call attention of a user to the endoscope image, according to a determination result inputted from the information management apparatus, and
the information management apparatus outputs, to the endoscope apparatus, a determination result indicating execution of the notification processing when an amount of inspection results each indicating abnormality of the inspection target in an inspection history satisfies the predetermined condition according to the instruction, the inspection history being a history of past inspections of the inspection target.

10. The endoscope system according to claim 9, wherein the information management apparatus includes a memory that stores an inspection history table including the inspection history.

11. A method of displaying an endoscope image, the method comprising:
acquiring an image of an inspection target;
displaying an endoscope image of the acquired inspection target; and
notification processing to call attention of a user to the endoscope image, according to an inspection history that is a history of past inspections of the inspection target,
wherein the notification processing is performed when an amount of inspection results each indicating abnormality of the inspection target in the inspection history satisfies a predetermined condition.

* * * * *